United States Patent [19]

Rose et al.

[11] Patent Number: 4,838,893
[45] Date of Patent: Jun. 13, 1989

[54] OXIDATION HAIR DYES COMPRISING SUBSTITUTED DIHYDROXYPYRIDINES AS COUPLING COMPONENTS

[75] Inventors: David Rose, Hilden; Norbert Maak, Neuss; Edgar Lieske, Düsseldorf, all of Fed. Rep. of Germany

[73] Assignee: Henkel Kommanditgesellschaft auf Aktien, Duesseldorf, Fed. Rep. of Germany

[21] Appl. No.: 65,142

[22] Filed: Jun. 24, 1987

Related U.S. Application Data

[63] Continuation of Ser. No. 816,952, Jan. 6, 1986, abandoned, which is a continuation of Ser. No. 583,144, Feb. 24, 1984, abandoned, which is a continuation of Ser. No. 349,835, Feb. 18, 1982, abandoned.

[30] Foreign Application Priority Data

Apr. 18, 1981 [DE] Fed. Rep. of Germany ....... 3115643

[51] Int. Cl.$^4$ .......................... A61K 7/06; A61K 7/13
[52] U.S. Cl. ............................................ 8/405; 8/407; 8/409; 8/421; 8/428; 132/208; 424/70
[58] Field of Search ................... 8/407, 409, 421, 428

[56] References Cited

U.S. PATENT DOCUMENTS 4,295,848 10/1981 Grollier et al. ..................... 8/421

FOREIGN PATENT DOCUMENTS 1486576 9/1977 United Kingdom .
1571570 7/1980 United Kingdom .

OTHER PUBLICATIONS

Rec. Trav. Chim. 63: 231, 1944.
Austral. J. Chem. 9: 244, 1956 (Ritchie).

*Primary Examiner*—Dale R. Ore
*Attorney, Agent, or Firm*—Ernest G. Szoke; Wayne C. Jaeschke; Norvell E. Wisdom, Jr.

[57] ABSTRACT

This invention is directed to compositions of the developer-coupler type of the dyeing of hair, consisting essentially of substituted dihydroxypyridine compounds or salts thereof as coupling components and, as developer components, the conventional components used in oxidation dyes.

22 Claims, No Drawings

OXIDATION HAIR DYES COMPRISING SUBSTITUTED DIHYDROXYPYRIDINES AS COUPLING COMPONENTS

This application is a continuation of application Ser. No. 816,952, filed 01/06/86, which is a continuation of Ser. No. 583,144, filed 02/24/84, which is a continuation of Ser. No. 349,835, filed 02/18/82, all three of which are abandoned.

FIELD OF THE INVENTION

This invention is directed to oxidation hair dyes. More specifically, this invention is directed to substituted dihydroxypyridines and their use as coupling components in oxidation hair dyes, especially those having tetraaminopyridines as developer components.

BACKGROUND OF THE INVENTION

Dyes known as oxidation dyes, which are produced by oxidative coupling of a developer component with a coupling component, are preferred due to their intense colors, the mild reaction conditions under which they are formed, and their very good fastness properties. Nitrogen bases such as p-phenylenediamine derivatives, diaminopyridines, 4-aminopyrazolone derivatives, and heterocyclic hydrazones are generally used as developer substances. Phenols, m-phenylenediamine derivatives, naphthols, resorcinol derivatives, and pyrazolones are useful as coupling components.

Good oxidation dyestuff components must meet the following requirements:

They must produce the desired color nuances in sufficient intensity during oxidative coupling with the respective developer or coupling component. Also, they must possess a capacity for being absorbed by human hair, which capacity ranges from sufficient to very good; and, in addition, they should be toxicologically and dermatologically safe. The production of the strongest possible color shades closely corresponding to the natural hair color nuances is also important. Furthermore, the general stability of the dyestuffs produced as well as their fastness to light and to washing and their thermostability, have very special significance for the prevention of color shifts from the original color nuance or even a change in color to different shades. In addition, in the hair dyeing business there is always an interest in new oxidation dye components that can be combined with the known dye components to produce new color nuances of cosmetic value.

Thus, the search for suitable oxidation hair dyes includes the task of finding the proper components that meet the above-mentioned prerequisites in an optimal fashion.

OBJECTS OF THE INVENTION

It is an object of the invention to provide substituted dihydroxypyridine compounds.

It is also an object of the invention to provide agents for the oxidative dyeing of hair that are based upon substituted dihydroxypyridine compounds as coupling components.

It is a further object of the invention to provide a process for dyeing hair wherein a novel hair dyestuff is employed.

These and other objects of the invention will become more apparent in the discussion below.

DETAILED DESCRIPTION OF THE INVENTION

Applicants have found novel hair dyestuffs that satisfy the above-mentioned requirements. The hair dyestuffs are based upon oxidation dyes comprising substituted dihydroxypyridine compounds of the formula

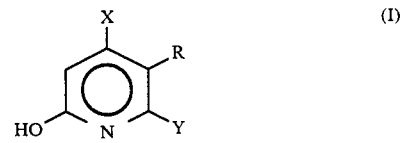

wherein R represents an alkyl or hydroxyalkyl having from 1 to 4 carbon atoms and X and Y each represent a hydroxyl group or an alkyl having from 1 to 4 carbon atoms, with the proviso that one of X and Y will represent a hydroxyl group and the other will represent an alkyl, or salts thereof with inorganic or organic acids, as coupling component, and, as developer component, one or more of the conventional developer substances used in oxidation hair dyes. Such hair dyestuffs can meet the above-mentioned requirements to an especially high degree and consequently represent especially valuable combinations in the area of oxidation hair dyes.

The dihydroxypyridines to be used as coupling components according to the invention are themselves well-known compounds and can be prepared by methods known from the literature. For example, the preparation of 2,6-dihydroxy-3,4-dimethylpyridine as well as 2,4-dihydroxy-5,6-dimethylpyridine was described in Rec. Trav. Chim. 63: 231, 1944, the preparation of 2,6-dihydroxy-3-ethyl-4-methylpyridine in Helv. Chim. Acta 2: 338, 1981, and the preparation of 2,6-dihydroxy-3-β-hydroxyethyl-4-methylpyridine in Austral. J. Chem. 9: 244, 1956. The use of the dihydroxypyridines according to the invention as component in hair dye products is new and cannot be deduced from publications of the state of the art.

Upon the use of the compounds according to the invention, that is, the substituted dihydroxypyridine compounds of Formula I and the salts thereof, as coupling components together with developers generally used for oxidation hair dyes, the resulting hair dyes yield very intense shades in the yellow to blue-brown range, and thus such use represents a considerable expansion of the possibilities in oxidation hair dyeing. In addition, the compounds according to the invention are characterized by very good fastness characteristics of the resulting colors, good solubility in water, good shelf-life, and toxicological as well as dermatological safety. The above particularly applies to compounds of Formula I wherein R represents a methyl, ethyl, or 2-hydroxyethyl group and one of X and Y represents a hydroxyl group and the other of X and Y represents a methyl group.

Especially bright, mainly yellow shades are obtained with the use according to the invention of the substituted dihydroxypyridines of Formula I as coupling components in oxidation hair dyes, when a tetraaminopyrimidine derivative of the general formula

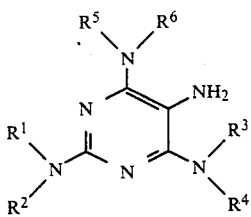

(II)

wherein $R^1$ to $R^6$ may each be a hydrogen atom; an alkyl moiety with from 1 to 4 carbon atoms; or the redical —$(CH_2)_nX$ in which n is an integer of from 1 to 4 and X is selected from the group consisting of a hydroxyl group, a halogen atom, and —$NR^7R^8$ in which $R^7$ and $R^8$ are each a hydrogen atom or an alkyl group having from 1 to 4 carbon atoms or together with the nitrogen atom $R^7$ and $R^8$ form a 5- or 6-membered heterocyclic ring of carbon atoms and the nitrogen atom, optionally containing an additional nitrogen or oxygen atom in the ring in place of a carbon atom, or each of $R^1$ and $R^2$, $R^3$ and $R^4$, and $R^5$ and $R^6$ may with the nitrogen atom to which they are attached form a 5- or 6-membered heterocyclic ring of carbon atom and the nitrogen atom, optionally containing an additional nitrogen or oxygen atom in the ring in place of a carbon atom, or an inorganic or organic salt thereof, is used as developer component.

The compounds 2,4,5,6-tetraaminopyrimidine and its derivatives are known as developer components in hair dyes from U.S. Pat. No. Re. 30,199, incorporated herein by reference. The dihydroxypyridines according to the invention are valuable yellow coupling substances in hair dye products using this type of developer.

In a particular embodiment of the invention, the dihydroxypyridines to be used according to the invention are used simultaneously with 2,4,5,6-tetraaminopyrimidine or derivatives thereof as developer and 2-chloro-6-methyl-3-aminophenol as blue coupling agent in hair dye products. 2-Chloro-6-methyl-3-aminophenol is a very valuable blue coupling agent in hair dye products based upon 2,4,5,6-tetraaminopyridmidines as developer. However, in combination with a known yellow coupling agent for this system, for example, 2,7-dihydroxynaphthalene, 6-hydroxyquinoline, or 8-amino-6-methoxyquinoline, the colors obtained are mainly of a bluish hue.

The use according to the invention of the substituted dihydroxypyridine as yellow coupling agents in combination with 2-chloro-6-methyl-3-aminophenol as blue coupling agent in hair dye products based upon 2,4,5,6-tetraaminopyrimidine derivatives as developer results in bright yellow-green and olive nuances without any bluish hue.

The substituted dihydroxypyridines of Formula I to be used as coupling components according to the invention can be used either as such or in the form of their salts with inorganic or organic acids, for example, as chlorides, sulfates, phosphates, acetates, propionates, lactates, or citrates. In addition, the substituted dihydroxypyridines to be used according to the invention can also be used together with additional, known coupling components in hair dye products. Examples of such known coupling agents include resorcinol, 2-methylresorcinol, 4-chlororesorcinol, and 2,4-dichloro-3-aminophenol.

The developer components to be used according to the invention are those that are conventionally used in oxidatively coupled dyestuffs, including the aforementioned compounds of Formula II. Examples of such developer components include primary aromatic amines with an additional functional group in the p-position, such as p-phenylenediamine, p-toluylenediamine, p-aminophenol, N-methyl-p-phenylenediamine, N,N-dimethyl-p-phenylenediamine, N,N-diethyl-2-methyl-p-phenylenediamine, N-ethyl-N-hydroxyethyl-p-phenylenediamine, chloro-p-phenylenediamine, N,N-bis-hydroxyethylamino-p-phenylenediamine, methoxy-p-phenylenediamine, 2,5-diaminoanisole, 2,6-dichloro-p-phenylenediamine, 2-chloro-6-bromo-p-phenylenediamine, 2-chloro-6-methyl-p-phenylenediamine, and 6-methoxy-3-methyl-p-phenylenediamine, and other compounds of this type which also contain one or more additional functional groups such as hydroxyl groups, amino groups, or —NHR or —$NR_2$ groups, in which R represents an alkyl or a hydroxyalkyl moiety with from 1 to 4 carbon atoms. Diaminopyridine derivatives, heterocyclic hydrazone derivatives such as 1-methyl-pyrrolidon-(2)-hydrazone, 4-aminopyrazolone derivatives such as 4-amino-1-phenyl-3-carbamoylpyrazolone-5, and N-butyl-N-sulfobutyl-p-phenylenediamine are additional examples of useful developer components.

Examples of the above-mentioned developer type of the tetraaminopyrimidines of Formula II, which also can be used as such or in the form of their salts with inorganic or organic acids, for example, as chlorides, sulfates, phosphates, acetates, propionates, lactates, or citrates, and which are advantageously used together with substituted dihydroxypyridines of Formula I in hair dye products, include the following:

2,4,5,6-tetraaminopyrimidine,
4,5-diamino-2,6-bismethylaminopyrimidine,
2,5-diamino-4,6-bismethylaminopyrimidine,
4,5-diamino-6-butylamino-2-dimethylaminopyrimidine,
2,5-diamino-4-diethylamino-6-methylaminopyrimidine,
4,5-diamino-6-diethylamino-2-dimethylaminopyrimidine,
4,5-diamino-2-diethylamino-6-methylaminopyrimidine,
4,5-diamino-2-dimethylamino-6-ethylaminopyrimidine,
4,5-diamino-2-dimethylamino-6-isopropylaminopyrimidine,
4,5-diamino-2-dimethylamino-6-methylaminopyrimidine,
4,5-diamino-6-dimethylamino-2-methylaminopyrimidine,
4,5-diamino-2-dimethylamino-6-propylaminopyrimidine,
2,4,5-triamino-6-dimethylaminopyrimidine,
4,5,6-triamino-2-dimethylaminopyrimidine,
2,4,5-triamino-6-methylaminopyrimidine,
4,5,6-triamino-2-methylaminopyrimidine,
4,5-diamino-2-dimethylamino-6-piperidinopyrimidine,
2,4,5-triamino-6-piperidinopyrimidine,
2,4,5-triamino-6-anilinopyrimidine,
2,4,5-triamino-6-benzylaminopyrimidine,
2,4,5-triamino-6-benzylidenaminopyrimidine,
4,5-diamino-6-methylamino-2-piperidinopyrimidine,
4,5,6-triamino-2-piperidinopyrimidine,
2,4,6-trismethylamino-5-aminopyrimidine,
2,4,5-triamino-6-di-n-propylaminopyrimidine,
2,4,5-triamino-6-morpholinopyrimidine,
2,5,6-triamino-4-dimethylaminopyrimidine,
4,5,6-triamino-2-morpholinopyrimidine,
2,4,5-triamino-6-β-hydroxyethylaminopyrimidine, 4,5,6-triamino-2-β-amino-ethylaminopyrimidine,
2,5,6-triamino-4-β-methylamino-ethylaminopyrimidine,
2,5-diamino-4,6-bis-γ-diethylamino-propylaminopyrimidine,
4,5-diamino-2-methylamino-6-β-hydroxy-ethylaminopyrimidine,
5-amino-2,4,5-triethylaminopyrimidine, and
2,4-bis-β-hydroxyethylamino-6-anilino-5-aminopyrimidine.

In the hair dyestuffs according to the invention, the coupling and developer components generally are used in approximately equimolar amounts. Although the equimolar use proves suitable, it is not disadvantageous to add the coupling component in a certain excess or deficiency. For example, the coupling and developer components can be present in a molar range of from about 2:1 to 1:2, a 10% or less excess or deficiency being preferred.

In addition, it is not necessary that the developer component and the coupling substance are homogeneous or pure products. On the contrary, the developer component may consist of mixtures of the developer compounds to be used according to the invention, and the coupling substance may be in the form of mixtures of substituted dihydroxypyridines or salts thereof according to the invention. Furthermore, the hair dyestuffs according to the invention may also contain, if desired, conventional, directly applicable dyes in the mixture, provided that such are necessary for the creation of certain color nuances.

The oxidative coupling, that is, the development of the dye, can in principle be carried out with atmospheric oxygen as is done with other oxidation hair dyestuffs also. However, chemical oxidation agents are advantageously employed. Particularly suitable as such oxidation agents are hydrogen peroxide or its addition compounds with urea, melamine, or sodium borate as well as mixtures of such hydrogen peroxide adducts with potassium peroxydisulfate.

Here, the tetraaminopyrimidines offer the advantage as developer component that they yield completely satisfactory dye results even with oxidative coupling by atmospheric oxygen, and that damage to the hair due to oxidation agents used otherwise for the oxidative coupling is consequently prevented. If, however, a lightening effect on the hair is desired together with the dye, the simultaneous use of oxidation agents is necessary.

The hair dyes according to the invention are incorporated into respective cosmetic preparations such as creams, emulsions, gels, or also simple solutions for their use and are mixed with one of the mentioned oxidation agents immediately before application to the hair. The concentration of the coupling/developer combination in such dyes is from about 0.2 to 5 percent by weight, preferably from about 1 to 3 percent by weight, based on the total weight of the preparation.

For the preparation of creams, emulsions, or gels, the dye components are mixed with the other components normally used in such preparations. Such additional components include, for example, wetting or emulsifying agents of the anionic or nonionic type such as alkylbenzenesulfonates, sulfates of fatty alcohols, higher alkylsulfonates, alkanolamides of fatty acids adducts of ethylene oxide onto fatty alcohols, thickeners such as methyl cellulose, starch, higher fatty alcohols, paraffin oil, and fatty acids, and perfume oils and hair-conditioning and grooming agents such as pantothenic acid and cholesterol. The mentioned additives are added in the amounts normal for these purposes. For example, wetting and emulsifying agents can be present in concentrations of from about 0.5 to 30 percent by weight, preferably from about 1 to 15 percent by weight, and thickeners can be present in concentrations of from about 0.1 to 25 percent by weight, preferably from about 1 to 15 percent by weight, based, respectively, on the weight of the total preparation.

A hair dye according to the invention can be applied in a weakly acid, neutral or particularly alkaline medium at a pH of 8 to 10, regardless of whether it is in the form of a solution, an emulsion, a cream, or a gel. The application temperatures range from about 15° to 40° C., preferably at room temperature. After the dye is allowed to react for approximately 30 minutes, the preparation is removed by rinsing from the dyed hair. The hair is washed with a mild shampoo and dried. The hair, which can be any color or length, can be either "live" hair or hair that has been cut, such as that in a wig.

The colors that can be achieved with the hair dyes according to the invention cover a broad spectrum of yellow to blue-brown shades, with the use of various developer and coupling components. The colors obtained show good fastness to light, shampooing, and abrasion, and they are easily stripped with reducing agents.

The following examples are intended to illustrate the invention and are not to be construed as limiting the invention thereto.

EXAMPLES

The following compounds of formula I were used as coupling components below in oxidation hair dyes:
K-1: 2,6-dihydroxy-3,4-dimethylpyridine
K-2: 4,6-dihydroxy-2,3-dimethylpyridine
K-3: 2,6-dihydroxy-3-ethyl-4-methylpyridine
K-4: 2,6-dihydroxy-3-(2-hydroxyethyl)-4-methylpyridine The following substances were used as developer components:
E-1: p-toluylenediamine
E-2: p-phenylenediamine
E-3: 2-chloro-p-phenylenediamine
E-4: 2,5-diaminoanisole
E-5: N,N-bis-2-hydroxyethyl-1-phenylenediamine
E-6: N-2-methoxyethyl-p-phenylenediamine
E-7: N-2-hydroxyethyl-p-phenylenediamine
E-8: N-2-hydroxypropyl-p-phenylenediamine
E-9: N-methyl-p-phenylenediamine
E-10: N-butyl-N-sulfobutyl-p-phenylenediamine
E-11: 2,4,5,6-tetraaminopyrimidine
E-12: 2-piperidino-4,5,6-triaminopyrimidine
E-13: 2-morpholino-4,5,6-triaminopyrimidine.

Procedure:

The hair dyes according to the invention were used in the form of a cream emulsion. For this, 0.01 mol of each of the developer substances and coupling substances listed in the table below were worked into an emulsion containing 10 parts by weight of fatty alcohols having 12 to 18 carbon atoms, 10 parts by weight of fatty alcohol sulfate (sodium salt) having 12 to 18 carbon atoms, and 75 parts by weight of water.

Then the pH of the emulsion was adjusted to 9.5 with ammonia, and the emulsion was made up to 100 parts by weight with water. Oxidative coupling was carried out with a 3% hydrogen peroxide solution acting as oxidation agent, 10 parts by weight of the hydrogen peroxide solution being added to 100 parts by weight of the emulsion.

After addition of the oxidation agents, the particular dyeing cream, with additional oxidation agent, was applied to standardized human hair which was 90% grey and which had not been specially pretreated, and the cream was left on the hair for 30 minutes at room temperature. After completion of the dyeing process, the hair was washed out with a conventional commercial shampoo and dried. The colorations obtained by this process are complied in the table below:

TABLE 1

| Example | Coupling Agent | Developer | Shade of Dyed Hair after Oxidation with 3% $H_2O_2$ Soluton |
|---|---|---|---|
| 1 | K-1 | E-1 | violet-brown |
| 2 | K-1 | E-2 | violet-grey |
| 3 | K-1 | E-3 | red-brown |
| 4 | K-1 | E-4 | nutria |
| 5 | K-1 | E-5 | blue-grey |
| 6 | K-1 | E-6 | olive-grey |
| 7 | K-1 | E-7 | green-grey |
| 8 | K-1 | E-8 | olive |
| 9 | K-1 | E-9 | green-grey |
| 10 | K-1 | E-10 | green-grey |
| 11 | K-1 | E-11 | yellow |
| 12 | K-1 | E-12 | yellow |
| 13 | K-1 | E-13 | yellow |
| 14 | K-2 | E-11 | sand yellow |
| 15 | K-3 | E-11 | canary yellow |
| 16 | K-4 | E-11 | yellow |
| 17 | K-2 | E-1 | eggplant-blue |

The special suitability of the use according to the invention of the substituted dihydroxypyridines as yellow coupling component in oxidation hair dye products with 2,4,5,6-tetraaminopyrimidine derivatives as developer component is apparent from the Examples Nos. 11 to 16.

The special suitability of the use of the substituted dihydroxypyridines as yellow coupling component according to the invention with 2-chloro-6-methyl-3-aminophenol hydrochloride as blue coupling agent in oxidation hair dye products with 2,4,5,6-tetraaminopyrimidine derivatives as developer component is demonstrated by the following Examples Nos. 18 to 29 set forth in Table 2 below.

Preparation of 2-Chloro-6-methyl-3-aminophenol hydrochloride (K-8)

Fourteen grams of 2-chloro-6-methyl-3-nitrophenol, which had been prepared according to the procedure set forth in Annalen der Chemie 417: 246, 1981, were catalytically hydrogenated in 50 ml ethanol, in the presence of a Raney-nickel catalyst. After the hydrogen uptake was complete, the catalyst was removed by filtration. The solution was acidified with hydrochloric acid and evaporated to dryness. The 2-chloro-6-methyl-3-aminophenyl hydrochloride was obtained in the form of white crystals with a melting point of 163° C.

The following generally known coupling components, which result in yellow shades with 2,4,5,6-tetraaminopyrimidine as developer, were used for comparison:
K-5: 2,7-dihydroxynaphthalene
K-6: 6-hydroxyquinoline
K-7: 8-amino-6-methoxyquinoline.

The comparison experiments were performed with a dye cream emulsion of the following composition:

10.2 gm of $C_{16}$-$C_{18}$-tallow fatty alcohol;
2.4 gm of $C_{12}$-$C_{18}$-coconut oil fatty alcohol;
30.6 gm of $C_{12}$-$C_{14}$-fatty alcohol diglycol ether sulfate (28 wt. % solution, TEXAPON N 25 ®, available from Henkel KGaA)
0.0025 mol of 2,4,5,6-tetraaminopyrimidine sulfate;
0.0025 mol of coupling combination (see, Table 2); and
57 gm of water and ammonia to a pH of 9.5.

The preparation of the dye cream, the oxidative coupling with 3% solution of hydrogen peroxide, the dyeing of the standardized hair that was 90% grey, and the washing of the hair with a commercial shampoo were carried out as described above for Examples 1 to 17.

Mixtures of 2-chloro-6-methyl-3-aminophenol hydrochloride (K-8) and known yellow coupling agents K-5 to K-7 as well as the new yellow coupling agent K-1 were used as coupling combination at various molar ratios. The results of such coupler component mixtures with 2,4,5,6-tetraaminopyrimidine sulfate as developer component are set forth in the following table:

TABLE 2

| Example | Coupler Combination | Molar Mixing Ratio | Shade of Dyed Hair after Oxidation with $H_2O_2$ Solution |
|---|---|---|---|
| 18 | K-8:K-5 | 7:3 | blue |
| 19 | K-8:K-5 | 5:5 | blue |
| 20 | K-8:K-5 | 3:7 | blue-grey |
| 21 | K-8:K-6 | 7:3 | blue |
| 22 | K-8:K-6 | 5:5 | blue |
| 23 | K-8:K-6 | 3:7 | grey-green |
| 24 | K-8:K-7 | 7:3 | blue |
| 25 | K-8:K-7 | 5:5 | blue |
| 26 | K-8:K-7 | 3:7 | olive green |
| 27 | K-8:K-1 | 7:3 | turquoise |
| 28 | K-8:K-1 | 5:5 | olive |
| 29 | K-8:K-1 | 3:7 | yellow-green |

It can be seen from the above table that whereas the coupler combinations employing known yellow coupling agents K-5 to K-7 resulted in blue dominant shades, the coupler combinations of Examples 27 to 29 did not.

The preceding specific embodiments are illustrative of the practice of the invention. It is to be understood, however, that other expedients known to those skilled in the art or disclosed herein, may be employed without departing from the spirit of the invention or the scope of the appended claims.

We claim:
1. An aqueous oxidation hair dye composition for the dyeing of human hair, comprising:
(A1) at least one first coupler consisting essentially of a compound of the formula

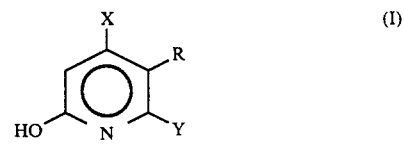

(I)

wherein
R is a $C_{1-4}$alkyl or hydroxyalkyl, and
one of X or Y is hydroxyl and the other is a $C_{1-4}$alkyl, or a salt of such compound with an inorganic or organic acid;
(A2) a second coupler which is 2-chloro-6-methyl-3-aminophenol;

(B) at least one developer, consisting essentially of a compound of the formula

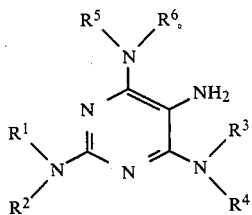

wherein (1) $R^1$ to $R^6$ are, independently, H, $C_{1-4}$alkyl, or $-(CH_2)_nX$ in which n is an integer from 1 to 4 and X is OH, a halogen, or $-NR^7R^8$ in which $R^7$ and $R^8$ are, independently, H, or a $C_{1-4}$ alkyl, or in which $R^7$ and $R^8$, together with a nitrogen, form a 5- or 6-membered heterocyclic ring which may contain an additional nitrogen or an oxygen replacement for a carbon;

(2) each of $R^1$ and $R^2$, $R^3$ and $R^4$, or $R^5$ and $R^6$, may form a 5- or 6-membered heterocyclic ring which may contain an additional nitrogen or oxygen replacement for a carbon; or (3) an acid salt thereof; and wherein the mol ratio (A1+A2):(B) is 0.5-2:1.

2. The composition of claim 1 wherein R is methyl, ethyl, or 2-hydroxyethyl, and either X or Y is methyl.

3. The composition of claim 1 wherein (A1) is at least one of:
2,6-dihydroxy-3,4-dimethylpyridine,
4,6-dihydroxy-2,3-dimethylpyridine,
2,6-dihydroxy-3-ethyl-4-methylpyridine, or
2,6-dihydroxy-3-(2-hydroxyethyl)-4-methylpyridine.

4. The composition of claim 1 wherein (B) is at least one of:
p-toluylenediamine,
p-phenylenediamine,
2-chloro-p-phenylenediamine,
2,5-diaminoanisole,
N,N-bis-2-hydroxyethyl-1-phenylenediamine,
N-2-methoxyethyl-p-phenylenediamine,
N-2-hydroxyethyl-p-phenylenediamine,
N-2-hydroxypropyl-p-phenylenediamine,
N-methyl-p-phenylenediamine,
N-butyl-N-sulfobutyl-p-phenylenediamine,
2,4,5,6-tetraaminopyrimidine,
2-piperidino-4,5,6-triaminopyrimidine, or
2-morpholino-4,5,6-triaminopyrimidine.

5. The composition of claim 3 wherein (B) is at least one of:
p-toluylenediamine,
p-phenylenediamine,
2-chloro-p-phenylenediamine,
2,5-diaminoanisole,
N,N-bis-2-hydroxyethyl-1-phenylenediamine,
N-2-methoxyethyl-p-phenylenediamine,
N-2-hydroxyethyl-p-phenylenediamine,
N-2-hydroxypropyl-p-phenylenediamine,
N-methyl-p-phenylenediamine,
N-butyl-N-sulfobutyl-p-phenylenediamine,
2,4,5,6-tetraaminopyrimidine,
2-piperidino-4,5,6-triaminopyrimidine, or
2-morpholino-4,5,6-triaminopyrimidine.

6. The composition of claim 1 wherein (B) is at least one of:
2,4,5,6-tetraaminopyrimidine,
4,5-diamino-2,6-bismethylaminopyrimidine,
2,5-diamino-4,6-bismethylaminopyrimidine,
4,5-diamino-6-butylamino-2-dimethylaminopyrimidine,
2,5-diamino-4-diethylamino-6-methylaminopyrimidine,
4,5-diamino-6-diethylamino-2-dimethylaminopyrimidine,
4,5-diamino-2-diethylamino-6-methylaminopyrimidine,
4,5-diamino-2-dimethylamino-6-ethylaminopyrimidine,
4,5-diamino-2-dimethylamino-6-isopropylaminopyrimidine,
4,5-diamino-2-dimethylamino-6-methylaminopyrimidine,
4,5-diamino-6-dimethylamino-2-methylaminopyrimidine,
4,5-diamino-2-dimethylamino-6-propylaminopyrimidine,
2,4,5-triamino-6-dimethylaminopyrimidine,
4,5,6-triamino-2-dimethylaminopyrimidine,
2,4,5-triamino-6-methylaminopyrimidine,
4,5,6-triamino-2-methylaminopyrimidine,
4,5-diamino-2-dimethylamino-6-piperidiniopyrimidine,
2,4,5-triamino-6-piperidinopyrimidine,
2,4,5-triamino-6-anilinopyrimidine,
2,4,5-triamino-6-benzylaminopyrimidine,
2,4,5-triamino-6-benzylidenaminopyrimidine,
4,5-diamino-6-methylamino-2-piperidinopyrimidine,
4,5,6-triamino-2-piperidinopyrimidine,
2,4,6-trismethylamino-5-aminopyrimidine,
2,4,5-triamino-6-di-n-propylaminopyrimidine,
2,4,5-triamino-6-morpholinopyrimidine,
2,5,6-triamino-4-dimethylaminopyrimidine,
4,5,6-triamino-2-morpholinopyrimidine,
2,4,5-triamino-6-β-hydroxyethylaminopyrimidine,
4,5,6-triamino-2-β-amino-ethylaminopyrimidine,
2,5,6-triamino-4-β-methylamino-ethylaminopyrimidine,
2,5-diamino-4,6-bis-γ-diethylaminopropylaminopyrimidine,
4,5-diamino-2-methylamino-6-β-hydroxyethylaminopyrimidine,
5-amino-2,4,5-triethylaminopyrimidine, or
2,4-bis-β-hydroxyethylamino-6-anilino-5-aminopyrimidine.

7. The composition of claim 6 wherein (A1) is at least one of:
2,6-dihydroxy-3,4-dimethylpyridine,
4,6-dihydroxy-2,3-dimethylpyridine,
2,6-dihydroxy-3-ethyl-4-methylpyridine, or
2,6-dihydroxy-3-(2-hydroxyethyl)-4-methyl-pyridine.

8. The composition of claim 1 in admixture with (A3) at least one third coupler, which is resorcinol, 2-methylresorcinol, 4-chlororesorcinol, or 2,4-dichloro-3-aminophenol.

9. The composition of claim 5 in admixture with (A3) at least one third coupler, which is resorcinol, 2-methylresorcinol, 4-chlororesorcinol, or 2,4-dichloro-3-aminophenol.

10. The composition of claim 1 wherein (A1), (A2), and (B) are about 0.2 to 5% by weight of the total weight of the aqueous hair dye composition.

11. The composition of claim 1 wherein (A1), (A2), and (B) are about 1 to 3% by weight of the total weight of the aqueous hair dye composition.

12. The composition of claim 1 wherein the mol ratio (A1+A2):(B) is about 1:1.

13. The composition of claim 1 wherein the mol ratio (A):(A2) is about 0.43-2.3:1.

14. A method for the dyeing of human hair comprising applying to said hair, a hair-dye effective amount of the composition of claim 1, said composition being at a temperature of about 15° C. to 40° C., and maintaining said composition on said hair for approximately 30 minutes.

15. A method for the dyeing of human hair comprising preparing a mixture of the composition of claim 1 with (C) a chemical oxidation agent, applying a hair-dye effective amount of said mixture to said hair, said mixture being at a temperature of about 15° C. to 40° C., and maintaining said mixture on said hair for approximately 30 minutes.

16. A method for the dyeing of human hair comprising preparing a mixture of the composition of claim 2 with (C) a chemical oxidation agent, applying a hair-dye effective amount of said mixture to said hair, said mixture being at a temperature of about 15° C. to 40° C., and maintaining said mixture on said hair for approximately 30 minutes.

17. A method for the dyeing of human hair comprising preparing a mixture of the composition of claim 3 with (C) a chemical oxidation agent, applying a hair-dye effective amount of said mixture to said hair, said mixture being at a temperature of about 15° C. to 40° C., and maintaining said mixture on said hair for approximately 30 minutes.

18. A method for the dyeing of human hair comprising preparing a mixture of the composition of claim 4 with (C) a chemical oxidation agent, applying a hair-dye effective amount of said mixture to said hair, said mixture being at a temperature of about 15° C. to 40° C., and maintaining said mixture on said hair for approximately 30 minutes.

19. A method for the dyeing of human hair comprising preparing a mixture of the composition of claim 5 with (C) a chemical oxidation agent, applying a hair-dye effective amount of said mixture to said hair, said mixture being at a temperature of about 15° C. to 40° C., and maintaining said mixture on said hair for approximately 30 minutes.

20. The method for the dyeing of human hair comprising preparing a mixture of the composition of claim 6 with (C) a chemical oxidation agent, applying a hair-dye effective amount of said mixture to said hair, said mixture being at a temperature of about 15° C. to 40° C., and maintaining said mixture on said hair for approximately 30 minutes.

21. A method for the dyeing of human hair comprising preparing a mixture of the composition of claim 7 with (C) a chemical oxidation agent, applying a hair-dye effective amount of said mixture to said hair, said mixture being at a temperature of about 15° C. to 40° C., and maintaining said mixture on said hair for approximately 30 minutes.

22. A method for the dyeing of human hair comprising preparing a mixture of the composition of claim 8 with (C) a chemical oxidation agent, applying a hair-dye effective amount of said mixture to said hair, said mixture being at a temperature of about 15° C. to 40° C., and maintaining said mixture on said hair for approximately 30 minutes.

* * * * *